United States Patent [19]

Laco

[11] Patent Number: 5,529,383
[45] Date of Patent: Jun. 25, 1996

[54] POSTURE SUPPORT

[76] Inventor: Randall J. Laco, 703 Ninth St. Suite 201, Durham, N.C. 27705

[21] Appl. No.: 235,480

[22] Filed: Apr. 29, 1994

[51] Int. Cl.[6] ........................................ A62B 35/00
[52] U.S. Cl. .................................. 297/488; 297/485
[58] Field of Search ........................ 297/411.23, 411.29, 297/464, 460, 484, 485, 487, 488; 5/628; 128/869, 870, 876

[56] References Cited

U.S. PATENT DOCUMENTS

| | | | |
|---|---|---|---|
| 2,639,604 | 9/1954 | Hourruitiner | 297/485 |
| 2,741,412 | 4/1956 | Hinkle | 297/485 X |
| 4,093,307 | 6/1978 | McLennan | 297/485 |
| 4,238,135 | 12/1980 | Sandham | 297/468 |
| 4,537,446 | 8/1985 | Roney et al. | 297/468 X |
| 4,634,184 | 1/1987 | Hitson | 297/468 |
| 5,009,467 | 4/1991 | McCoy | 297/411.29 X |
| 5,148,563 | 9/1992 | Klearman et al. | 128/869 X |

*Primary Examiner*—Peter R. Brown
*Attorney, Agent, or Firm*—Terrance L. Siemens

[57] ABSTRACT

A device for retaining the user in a substantially upright position when seated in a chair is disclosed. The device consists of a bracket attached to the back of the chair having two distal ends, the ends extending laterally outward from the back support portion of the chair. Attached to these distal ends is an adjustable, padded strap that supports the abdomen of the person seated in the chair to prevent them from slouching or leaning forward. The strap extends perpendicular to the rear strut or frame of the chair to hold the user firmly in an upright position.

3 Claims, 1 Drawing Sheet

5,529,383

POSTURE SUPPORT

BACKGROUND OF THE INVENTION

1. Field of the Invention

The present invention relates to restraining devices. More specifically, it relates to a restraining device adapted to be attached to an existing chair for the purpose of holding the person seated in the chair in an upright position. Even more specifically, it relates to a device consisting of a detachable bracket that extends outwards from the back of the chair and that has attached thereto an adjustable strap for holding the user firmly upright against the back of the chair, thus preventing slouching during long periods of work done while seated.

2. Description of the Prior Art

More and more, people are working while seated at a desk, usually while entering data, using a word processor, or other enterprise. They remain seated for long stretches of time, and the tendency, in the types of chairs standardly employed in offices, is to slouch; that is to drop the shoulders and lean the torso towards the edge of the desk, computer screen, etc. This can lead to long term health problems in that backaches can be brought on by this position, and these backaches can become chronic, thus cutting into the productive time of the person or employee thus afflicted. The present invention seeks to address this problem by providing a padded, adjustable strap that extends perpendicular to the rear strut of the chair so that the person utilizing the device is held comfortably upright and is not allowed to slouch or lean forward. In a search in this art, the following patents were uncovered that appeared relevant to the present invention:

In U.S. Pat. No. 579,818 issued on Mar. 30, 1897 to Ella I. Cooley there is disclosed a safety belt. The device has a waist belt, a fastening strip for the device's attachment to a seat, and an elastic strip that connects the waist belt to the fastening strip. The belt of the patent is designed to restrain a child in a high chair while permitting limited movement. By contrast, the instant invention is for the purpose of maintaining correct posture and therefore does not have elastic straps and does not permit lateral or longitudinal movement of the torso with respect to the chair when properly fastened.

U.S. Pat. No. 2,799,322 issued on Jul. 16, 1957 to Roy D. Jordan discloses a child's safety seat for use in an automobile. The device has a tubular support frame for the seat, with the back portion having a floating type engagement with a rack. The rack is made of arcuate rod material and is designed to slip over the back of a car seat. The seat has a safety belt which serves to restrain the child against the existing automobile seat back during sudden deceleration. By contrast, the seat of this invention is not concerned with inertial loading and therefore has its own seat back with the rear belt attachment points being wider than the seat back.

Next is U.S. Pat. No. 3,957,304 issued on May 18, 1976 to L. John Koutsky et al. This discloses a flexible seat restraint where a tie is connected to the base of a shock absorbing seat suspension to prevent excessive deflection during a rollover. The belt of this patent is arranged as a pelvic restraint and is thus not suitable to maintain posture. By contrast, the combination seat and belt of the instant invention is intended as an upper torso restraint preventing improper posture.

In U.S. Pat. No. 4,706,992 issued on Nov. 17, 1987 to Deborah L. Downing et al. there is disclosed a seat belt that is pivotable to allow the user to recline upon the seat. The restraint belt fits primarily the pelvic region and does not attach to the seat back but rather to the existing automotive seat belt. By contrast, the instant invention has its own seat back with the rear belt attachment points being wider than the seat back and is intended as an upper torso restraint promoting proper posture.

U.S. Pat. No. 4,015,878 issued on Apr. 5, 1977 to Charles M. Perkins discloses a chair construction where the back portion has an upper and lower part. The upper part is vertically positionable and carries a torso girding belt to allow the user to at least partially elevate the torso from the seat. The torso girding strap of the patented seat is designed to support a portion of the user's weight as the upper seat part is ratcheted away from the lower part. By contrast, the instant invention is not intended to lift the user's weight with the strap and the strap is therefore not attached to a movable portion of the seat.

In U.S. Pat. No. 4,177,807 issued on Dec. 11, 1979 to John J. Ocel et al. there is disclosed a restraining belt for wheelchairs, stretchers, and the like. A flexible strap extends around the portion of the implement to which the patient is to be secured and a hook and loop fastener arrangement is disposed on the opposite side of the implement. A flexible fabric sleeve can be extended over the interengaging portions to obviate the accidental or intentional uncoupling of the strap. The strap of the patent is fastened out of reach of the user with the sleeve intended to positively prevent the user from disconnecting the strap. By contrast, the strap fastener of the instant invention is not meant as an involuntary restraint and is thus easily accessible to the user.

Lastly, U.S. Pat. No. 4,759,588 issued on Jul. 26, 1988 to Monte J. Husnik discloses a seat belt training cushion for automotive child seats. This device is an accessory seat cushion for partially camouflaging the buckled restraint with separate padded arms. The actual restraint straps of the patent are fitted around the pelvic area. By contrast, the present invention provides an upper torso restraint promoting proper posture in a static environment.

None of the above inventions and patents, taken either singly or in combination, is seen to describe the instant invention as claimed.

SUMMARY OF THE INVENTION

The present invention is a device for retaining the user in a substantially upright position when seated in a chair. The device consists of a bracket attached to the back of the chair having two distal ends, the ends extending laterally outward from the back support portion of the chair. Attached to these distal ends is an adjustable, padded strap that supports the upper abdomen or chest of the person seated in the chair to prevent them from slouching or leaning forward. The strap extends perpendicular to the rear strut or frame of the chair to hold the user firmly in an upright position. The plane of the strap, when correctly fastened, is substantially perpendicular to the torso and does not press against the sides of the user.

Accordingly, it is a principal object of the invention to provide a posture support device which overcomes the disadvantages of the prior art in a simple but effective manner.

Accordingly, it is another object of the invention to provide a posture support device comprising a chair and a strap that maintains the user in a comfortable and healthy upright position while seated.

It is another object of the invention to provide a posture support device that maintains the user in such a comfortable upright position with a strap which is easily attachable and detachable by the user.

It is another object of the invention to provide a posture support device that maintains the user in such a comfortable upright position without totally encircling the user or cutting off circulation.

It is another object of the invention to provide a posture support device that maintains the user in such an upright position with a strap which is attached to the seat back at positions wider than the torso of the user and wider than a conventional secretarial chair back rest.

It is another object of the invention to provide a posture support device wherein the strap is attached to a removable bracket that extends laterally outward from the portion of the chair that supports the user's back to assist in maintaining the user's posture.

It is another object of the invention to provide a posture support device which may be provided as a kit to convert an existing chair into a posture retaining chair or may be provided as an original article of manufacture in its entirety.

It is a further object of the invention to provide a posture support that includes a padded portion around the restraining strap for the comfort of the user.

Finally, it is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

Figure 1:
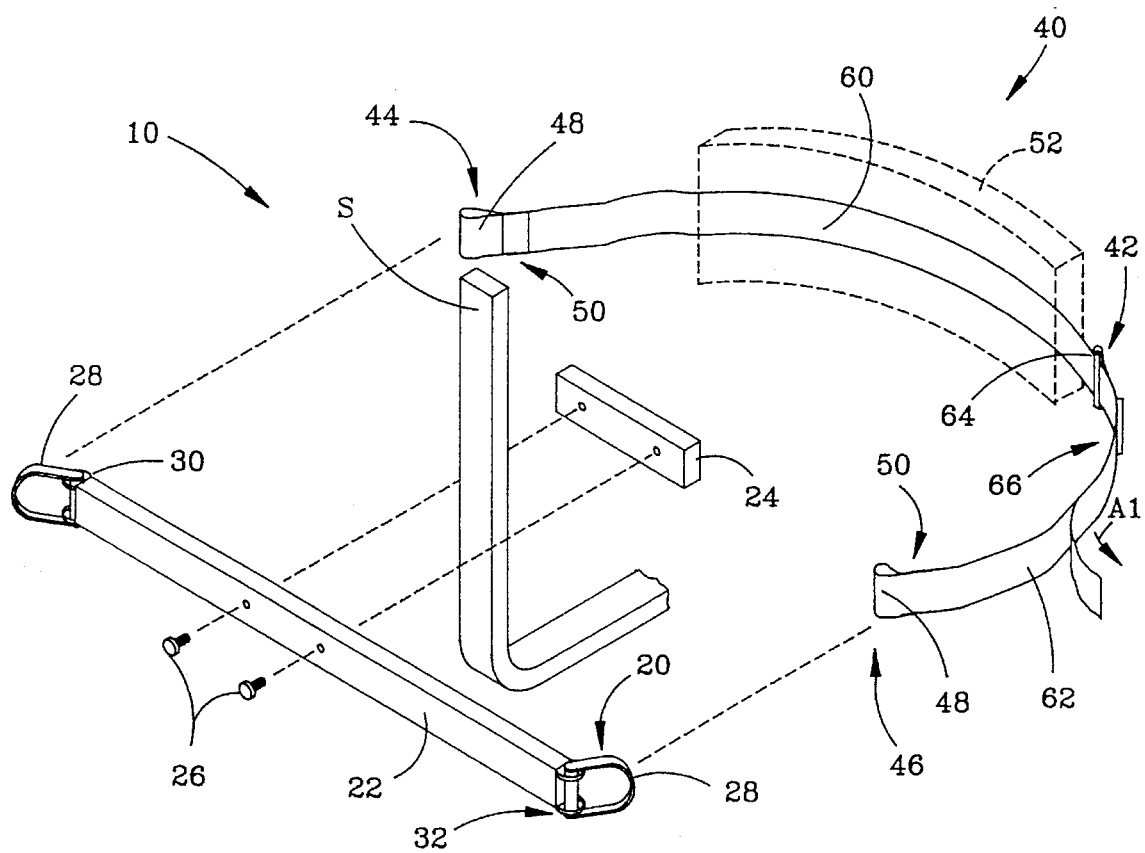
FIG. 1 is an exploded partial perspective view of an embodiment of the present invention adapted to be attached to the rear frame of a "secretary" type chair.

One preferred embodiment of the present invention is indicated in FIG. 1 generally at 10. In this embodiment the device 10 can be divided into two main portions. Bracket portion 20 consists of a posterior bracket member 22, an anterior bracket member 24, fastening means 26, shown as threaded bolts, and D-rings 28 at distal ends 30, 32 of the posterior bracket member 22. The posterior and anterior bracket members 22, 24 are attached to one another by the fastening means 26 such that the chair frame strut S lies between them. Thus the bracket portion 20 and the strap portion 40 (discussed hereinafter) are maintained in a predetermined relation with the chair.

Strap portion 40 consists of strap 42, strap ends 44, 46, and loop portions 48 that are formed by cooperating hook and loop type fasteners on the strap 42 as indicated at 50 in FIG. 1. The artisan will recognize that the hook and loop fasteners are but one way to fasten the ends of the strap to the D-rings at each end of bracket 22. The strap ends could obviously be permanently sewn or knotted in place if desired. Additionally, a padded portion 52 is disposed on one side of the strap 42. This padded area 52 (shown in broken lines in FIG. 1) is preferably made of a cushioned material such as foam rubber covered by nylon and is approximately four by twelve inches and a quarter of an inch thick. The padded area 52 provides comfort for the user over prolonged periods of time. Pad 52 may be made integral with strap 42 or the strap may be passed through a hemmed loop portion of the pad to allow for easy removal and cleaning of the pad. The strap 42 is adjustable. In the preferred embodiment, strap 42 is in two sections 60 and 62. Section 60 is attached at one end to a D-ring 28 and at the other terminates in a plastic or metal loop 64. Strap section 62 is also attached to a D-ring 28 and at the other end is passed through loop 64 and then is doubled back (as seen clearly in FIG. 1) where it secured to itself as indicated at 66. This self securement is preferably accomplished by means of cooperating hook and loop type fasteners. This arrangement allows the user to selectively adjust the overall length of the restraining strap, making it smaller by pulling the doubled back portion of strap section 62 in the direction indicated by arrow A1 in FIG. 1. It should be understood that the strap adjustment feature described above is only one of many various well-known ways in which a strap length can be preset or predetermined. Other means would be obvious to a skilled artificer and lie within the scope of the contemplated invention. In addition, it should be emphasized that the strap bracket 20 could be attached to the chair in other various ways, with the description given herein being primarily for the purposes of illustration of one preferred form of the inventive concept.

Figure 2:
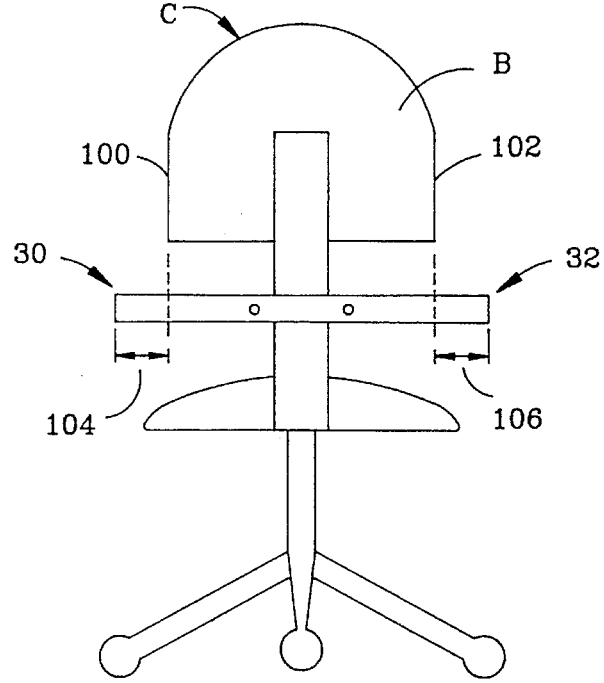
FIG. 2 is a rear view of the attached invention showing the extension of the bracket laterally beyond the back support portion of the chair.

Turning to FIG. 2, it can be seen that the distal ends 30, 32 of bracket portion 20 extend laterally out beyond the sides 100, 102 of the back portion B of the chair C as indicated by the lines 104 and 106 in FIG. 2. This has at least three purposes. Firstly, it prevents a user's inadvertent contact with the distal ends 30, 32 and the D-rings 28 (or other strap attachment means) thereon while the device is in use. Secondly, it provides a flatter angle between the front of the user relative to the plane generally described by the bracket portion 20. The strap portion 40 is therefore easier to remove from the bracket portion 20 if the device is not to be used. Thirdly, the strap encircles a smaller portion of the diameter of the torso thus not restricting circulation.

Also, in the preferred embodiment described herein, the bracket portion 20 is adjustable on or removable from the chair C by detachment of the fastening means 26. It is contemplated, however, that the bracket portion 20 of the device 10 could be permanently attached to a chair at the point of manufacture. It should also be understood that though a "secretary" type chair is shown here, other types of chairs could be enhanced by applicant's invention by modification of the bracket portion 20 and the fastening means 26.

It is to be understood that the present invention is not limited to the sole embodiment described above, but encompasses any and all embodiments within the scope of the following claims.

I claim:

1. A restraining device in combination with a chair having a back support portion, wherein the back support portion has two generally vertical lateral sides, said restraining device comprising:

a bracket portion attached to the back support portion of the chair, said bracket portion being a rigid bar generally horizontally disposed and including two distal ends, each said distal end extending laterally beyond the lateral sides of the back portion of the chair, said bracket portion comprising an anterior bracket member, a posterior bracket member, and fastening means for fixing said anterior bracket member and said posterior bracket member in a fixed relationship to the back portion of the chair such that the back portion of the chair is sandwiched between said anterior bracket member and said posterior bracket member;

strap attachment means located proximate to each one of said distal ends of said bracket portion; and a restraining strap connected to said bracket portion at each one of said distal ends of said bracket portion, said restraining strap including strap length adjustment means for setting a predetermined strap length, whereby a user seated in the chair adjusts said restraining strap such that the user's torso is held firmly against the back portion of the chair, thus preventing slouching and leaning during extended periods of work, and a pad attached to said restraining strap, for cushioning the front of the user.

2. The restraining device according to claim 10, wherein said fastening means comprise threaded fasteners.

3. A restraining device in combination with a chair having a back support portion, wherein the back support portion has two generally vertical lateral sides, said restraining device comprising:

a bracket portion attached to the back support portion of the chair, said bracket portion being generally horizontally disposed and including two distal ends, each said distal end extending laterally beyond the lateral sides of the back portion of the chair, said bracket portion comprising an anterior bracket member, a posterior bracket member, and a plurality of threaded fasteners for fixing said anterior bracket member and said posterior bracket member in a fixed relationship to the back portion of the chair such that the back portion of the chair is sandwiched between said anterior bracket member and said posterior bracket member;

strap attachment means located proximate to each one of said distal ends of said bracket portion; and a restraining strap connected to said bracket portion at each one of said distal ends of said bracket portion, said restraining strap including strap length adjustment means for setting a predetermined strap length, whereby a user seated in the chair adjusts said restraining strap such that the user's torso is held firmly against the back portion of the chair, thus preventing slouching and leaning during extended periods of work.

* * * * *